United States Patent
Hashiguchi et al.

(10) Patent No.: US 9,931,180 B2
(45) Date of Patent: Apr. 3, 2018

(54) DENTAL POWDER/LIQUID MATERIAL-CONTAINING PREPARATION ACCOMMODATION BAG AND DISPENSING METHOD FOR SAME

(71) Applicant: Tokuyama Dental Corporation, Tokyo (JP)

(72) Inventors: Masanao Hashiguchi, Tokyo (JP); Nobutoshi Yamaguchi, Tokyo (JP); Kei Nakashima, Tokyo (JP)

(73) Assignee: Tokuyama Dental Corporation, Tokyo (JP)

( * ) Notice: Subject to any disclaimer, the term of this patent is extended or adjusted under 35 U.S.C. 154(b) by 0 days.

(21) Appl. No.: 14/890,468

(22) PCT Filed: May 14, 2014

(86) PCT No.: PCT/JP2014/062819
§ 371 (c)(1),
(2) Date: Nov. 11, 2015

(87) PCT Pub. No.: WO2014/185449
PCT Pub. Date: Nov. 20, 2014

(65) Prior Publication Data
US 2016/0106519 A1    Apr. 21, 2016

(30) Foreign Application Priority Data
May 17, 2013 (JP) ................................. 2013-104819

(51) Int. Cl.
*B65D 25/08* (2006.01)
*A61C 5/06* (2006.01)
(Continued)

(52) U.S. Cl.
CPC ................ *A61C 5/068* (2013.01); *A61C 5/50* (2017.02); *A61C 5/60* (2017.02); *A61C 5/66* (2017.02);
(Continued)

(58) Field of Classification Search
CPC ......... A61C 5/068; A61C 5/06; A61C 19/005; A61C 13/00; A61C 5/66; A61C 5/68;
(Continued)

(56) References Cited

U.S. PATENT DOCUMENTS 3,722,833 A    3/1973    Shimizu
3,756,571 A    9/1973    Winberg
(Continued)

FOREIGN PATENT DOCUMENTS

EP    0513364    11/1992
JP    8508193 T2    9/1996
(Continued)

OTHER PUBLICATIONS

Extended European Search Report dated Oct. 12, 2016 issued in the corresponding European patent application No. 14797320.0.
(Continued)

*Primary Examiner* — J. Gregory Pickett
*Assistant Examiner* — Rafael Ortiz
(74) *Attorney, Agent, or Firm* — Rankin, Hill & Clark LLP

(57) ABSTRACT

A dental powder/liquid material-containing preparation accommodation bag, which suppresses entrainment of air in mixing a powder material and a liquid material for dispensing, is provided. A powder material 8 is accommodated in a powder material accommodation chamber 3 of a bag body 2, while a liquid material 9 dissolving the powder material 8 and changing into a pasty form, in cooperation with the powder material 8 is accommodated in a liquid material
(Continued)

accommodation chamber 4 partitioned from the powder material accommodation chamber 3 by a weakened section 7. The weakened section 7 is ruptured by applying a pressing force to the bag body 2. As a result, the powder material accommodation chamber 3 and the liquid material accommodation chamber 4 communicate, to feed the liquid material accommodated in the liquid material accommodation chamber 4 into the powder material accommodation chamber 3. Then, the powder material 8 and the liquid material 9 changing into the pasty form are pressed within the powder material accommodation chamber 3 from the surfaces of the bag body 2 for dispensing.

6 Claims, 3 Drawing Sheets

(51) Int. Cl.
| | |
|---|---|
| *A61C 13/00* | (2006.01) |
| *B65D 81/32* | (2006.01) |
| *A61C 19/00* | (2006.01) |
| *A61C 5/50* | (2017.01) |
| *A61C 5/60* | (2017.01) |
| *A61C 5/66* | (2017.01) |
| *A61C 5/68* | (2017.01) |

(52) U.S. Cl.
CPC ............... *A61C 5/68* (2017.02); *A61C 13/00* (2013.01); *A61C 13/0024* (2013.01); *A61C 19/005* (2013.01); *B65D 81/3266* (2013.01); *A61C 2202/00* (2013.01); *A61C 2202/01* (2013.01)

(58) Field of Classification Search
CPC ........ A61C 5/60; A61C 5/50; B65D 81/3266; B65D 25/08
USPC .................................. 206/222, 63.5, 83, 368
See application file for complete search history.

(56) References Cited

U.S. PATENT DOCUMENTS

| | | | | |
|---|---|---|---|---|
| 5,219,897 | A * | 6/1993 | Murray | A61B 17/8833 433/228.1 |
| 5,398,483 | A | 3/1995 | Gilbert | |
| 5,710,194 | A | 1/1998 | Silver | |
| 7,906,565 | B2 * | 3/2011 | Hashiguchi | A61K 6/0026 523/120 |
| 2004/0078023 | A1 * | 4/2004 | Gollier | B65D 81/3266 604/410 |
| 2004/0176242 | A1 * | 9/2004 | Ishihama | C08F 10/00 502/113 |
| 2007/0080078 | A1 * | 4/2007 | Hansen | B65D 81/3266 206/219 |
| 2008/0083348 | A1 * | 4/2008 | Kuo | A61C 9/0026 106/35 |
| 2009/0234317 | A1 * | 9/2009 | Navarro | A61J 1/10 604/408 |
| 2012/0231250 | A1 * | 9/2012 | Minatoya | A23G 3/362 428/219 |

FOREIGN PATENT DOCUMENTS

| | | |
|---|---|---|
| JP | 2000506123 T2 | 5/2000 |
| JP | 2005231691 A2 | 9/2005 |
| JP | 2006526552 T2 | 11/2006 |
| JP | 3967488 B2 | 8/2007 |
| JP | 201083567 | 4/2010 |
| JP | 201163537 | 3/2011 |
| JP | 4693434 B2 | 6/2011 |
| JP | 201387076 | 5/2013 |

OTHER PUBLICATIONS

International Search report dated Jul. 29, 2014 filed in PCT/JP2014/062819.

* cited by examiner

DENTAL POWDER/LIQUID MATERIAL-CONTAINING PREPARATION ACCOMMODATION BAG AND DISPENSING METHOD FOR SAME

TECHNICAL FIELD

This invention relates to a dental powder/liquid material-containing preparation accommodation bag which enables a powder material and a liquid material to be easily dispensed with high quality; and a dispensing method therefor.

BACKGROUND ART

Among typical dental materials are dental fillings, dental adhesives, dental prostheses, and dental prosthesis repair materials. The dental fillings are materials for filling in holes which have been bored or drilled for treatment of decayed teeth. The dental prostheses are artificial materials (crowns, dentures) for restoration of defective teeth. The dental prosthesis repair materials refer to materials for repairing the above prostheses, and their examples include repair materials for tooth crowns, and repair materials for denture base materials.

An overwhelming number of such dental materials are composed of a plurality of components, and a plurality of the materials are mixed in situ and used by dentists or the like during treatment of patients. Combinations of these materials include combinations of liquid materials, combinations of powder materials and liquid materials, and combinations of paste materials.

Of these combinations, a combination of a powder material and a liquid material (a dental powder/liquid material) can utilize a sharp increase in viscosity produced by mixing the powder material and the liquid material. Generally, it is important for dental treatment that the treatment is completed promptly within a dental examination room (so as not to make the patient wait). Thus, it is important for the above material to be excellent in properties, such as shapability, appropriate property for building up with resin (handleability), and a quick finish (final change), as a dental material. Since these properties can be obtained by utilizing the above-mentioned sharp viscosity increase, the rapidity of the viscosity increase of the dental powder/liquid material is an important characteristic.

Typical examples of a powder material/liquid material combination among such dental powder/liquid materials are denture base liners, dental repair resins, tissue conditioners, and dental resin cements.

The denture base liner is a repair material which, when a denture mounted does not fit the oral mucosa because of bone resorption, deformation of the mucosal surface, or the like, liners the surface of the unfit denture base to render the denture fitting again.

The dental repair resin is a resin material for repairing a prosthesis, such as a fractured denture or a chipped artificial tooth, or for preparing a temporary crown for use temporarily at a defective site.

The tissue conditioner is a tacky conditioning material which, when the gingival mucosa hurts, for example, because a denture does not fit, is used in an area of close contact between the denture and the gingiva for recovery of the gingival mucosa. The tissue conditioner takes a final form of an elastic body under the conditions for its use.

The dental resin cement is a material which, in restoring a tooth having lost functions owing to a dental caries, an accident or the like, with the use of a metallic or ceramic material for crown restoration, called an inlay or crown, is used to fix the material for crown restoration to the tooth. This material is intended for firm adhesion of various adherends (metals, ceramics, etc.) as well as the tooth.

As the denture base liner and the dental repair resin, two-component materials composed of the following components, for example, are generally used: polymeric organic components such as polymethyl methacrylate (hereinafter also referred to as PMMA) polyethyl methacrylate (hereinafter also referred to as PEMA), and a copolymer of methyl methacrylate and ethyl methacrylate (hereinafter also referred to as P(MMA-EMA)); and monomer components such as radical polymerizable compounds, e.g., methyl methacrylate, ethyl methacrylate, butyl methacrylate, and 2-hydroxyethyl methacrylate.

Such a two-component material is composed of a powder material containing an organic polymer and a liquid material containing a monomer, and can be prepared by distributing a suitable polymerization initiator component. A radical polymerization initiator is frequently used as the polymerization initiator component for curing. Both types of components are mixed during dental examination, and the monomer is polymerized using the radical polymerization initiator, whereby a cured product can be obtained. When the monomer component used in the above two-component material is brought into contact with the polymer component, it dissolves a part of the polymer component in a short time and infiltrates into the polymer component to swell it. Thus, the viscosity of a mixture of the monomer component and the polymer component is moderately adjusted, whereby the advantage that a clinical or technical operation can be facilitated is produced (see Patent Document 1).

As the above-mentioned two-component materials, there are not only finally rigid cured products, but also finally elastic bodies like the denture base tissue conditioners. In this case, as the liquid materials, plasticizers in liquid form, typified by sebacic acid ester and phthalic acid ester, are used rather than monomers. High-molecular plasticizers are also used satisfactorily as the liquid plasticizers (see Patent Document 2).

Patent Document 3 discloses a flat bag comprising a film and having a partition portion nearly in the middle, wherein a dry nonwoven fabric is accommodated in one of the resulting compartments, while a cosmetic such as a facial lotion can be accommodated separately in the other compartment. The partition portion of the flat bag is formed by thermally fusing upper and lower parts of the film, which constitute the upper and lower surfaces of the bag, via a strip-shaped tape having releasability. Such a flat bag is configured such that the partition wall is ruptured, whereby the accommodation compartments communicate with each other, with the result that the nonwoven fabric is adequately infiltrated with the facial lotion.

PRIOR ART DOCUMENTS

Patent Documents

Patent Document 1: Japanese Patent No. 3967488
Patent Document 2: Japanese Patent No. 4693434
Patent Document 3: JP-A-2010-83567

SUMMARY OF THE INVENTION

Problems to be Solved by the Invention

As mentioned above, when the monomer and the liquid plasticizer used in the two-component material are contacted with the polymer component, they dissolve a part of the polymer component in a short time, and infiltrate into the polymer component to swell it. In using such a dental material, an operator such as a dentist weighs the monomer component, the liquid plasticizer component, and the polymer component, and if desired, a polymerization initiator. The polymerization initiator is often distributed into the powder material or the liquid material. A mixture of them is placed in a blending cup, where the mixture is kneaded by the operator using a spatula or a stirring rod manually. Upon kneading, the mixture turns into a highly flowable slurry, which further increases in viscosity, becoming a paste like a fresh mochi, rice cake. The operator processes it so that it becomes moderately hard. The mixture finally cures, but its final form may be an elastic body, without occurrence of a polymerization reaction, as in the aforementioned denture base tissue conditioner.

Operation using a spatula or the like, however, is apt to entrain air by kneading or stirring. The entrained air minimally escapes, imparting the nature characteristic of the dental material that air remains in the final product. That is, the powder material constituting the dental powder/liquid material has a large specific surface area and is bulky. Thus, the powder material has the property of easily taking air into voids between its particles, and tends to pose the problem of air remaining in the final product much more frequently than when a liquid material and another liquid material are mixed, or when a paste material and another paste material are mixed. Incorporation of air into the final product causes decreased strength or impaired aesthetics to dental materials. A radical curable composition, in particular, is liable to undergo a decrease in strength and discoloration or coloration due to long-term use. Since dental materials are also used in visible areas, their aesthetic properties are of utmost importance.

Patent Document 3, as described above, discloses the flat bag in which the dry nonwoven fabric is accommodated in one of the compartments, while the cosmetic such as a facial lotion can be accommodated separately in the other compartment.

The flat bag of Patent Document 3, however, has only the convenience of being able to mix the cosmetic with the nonwoven fabric at any time, and mixing them together does not bring about any improvement in the quality of the nonwoven fabric and the cosmetic. That is, the nonwoven fabric impregnated with the cosmetic in the flat bag, and the nonwoven fabric impregnated with the cosmetic outside the flat bag are equal in quality, and no quality improvement exists between them.

The present invention has been accomplished in the light of the circumstances mentioned above. It is an object of the invention to provide a dental powder/liquid material-containing preparation accommodation bag which, in mixing a powder material and a liquid material for dispensing, suppresses entrainment of air, is easy to handle, facilitates mixing, has ease of imparting a form (processing) with a prompt increase in viscosity, gives a quick finish, and brings about an improvement in quality by dispensing within a bag body, as compared with dispensing outside the bag body; and a dispensing method therefor.

Means for Solving the Problems

The present invention provides a packaged form of a dental composition which cures or shows property changes upon mixing of a plurality of components, wherein the respective components are packaged while being shut off from the outside, and the plurality of components are mixed out of contact with the outside.

This packaged form has compartments which can accommodate the respective components, and in which a wall portion separating the compartments from each other is blocked with weaker force than are other walls, the compartment containing one of the components is pressed to open the partition wall separating both compartments, thereby feeding the component accommodated in the compartment on the pressed side into the other compartment and, after both components are fed in, pressing is repeated on the compartment on the pressed side, whereby the plurality of components can be mixed.

That is, the object of the present invention is attained by a dental powder/liquid material-containing preparation accommodation bag, comprising: a bag body divided into a plurality of parts to form a plurality of sealed accommodation chambers; and a weakened section, formed between the accommodation chambers, for partitioning the accommodation chambers, the weakened section being formed to be rupturable by a pressing force applied to the bag body, the accommodation chambers being allowed to communicate after rupture of the weakened section, whereby contents accommodated in the accommodation chambers can be gathered within one of the accommodation chambers and can be mixed there, wherein the bag body is configured such that the plurality of accommodation chambers accommodate a dental powder/liquid material composed of a powder material containing an organic polymer, and a liquid material dissolving the powder material and changing into a pasty form in cooperation with the powder material, with the powder material and the liquid material being accommodated separately in the accommodation chambers, and the powder material and the liquid material changing into the pasty form after rupture of the weakened section can be pressed via the surfaces of the bag body.

The volume of air, at room temperature, of the dental powder/liquid material-containing preparation accommodation bag is preferably in the range of 10 to 45%, more preferably in the range of 15 to 40%, based on the volume of the accommodation chamber for gathering and mixing the contents accommodated within the accommodation chambers. If the volume of air is larger than the value defined above, incorporation of air bubbles into the paste is marked. If the volume of air is smaller than the value defined above, the work efficiency of blending of the powder material and the liquid material lowers.

The accommodation chamber for gathering and mixing the contents accommodated within the respective accommodation chambers preferably has an internal volume of 1 to 3 $cm^3$ relative to 1 g of a pasty substance obtained by blending the powder material and the liquid material.

The dental powder/liquid material is preferably in such a configuration that the powder material contains a powder of a lower alkyl(meth)acrylate polymer, the liquid material contains a monomer, at least one of the powder material and the liquid material contains a polymerization initiator, and the final form of the powder material and the liquid material changing into the pasty form is a cured product. The cured product can be applied effectively to a denture base liner, a dental repair resin, and a dental resin cement. The dental powder/liquid material is also preferably in such a configuration that the powder material contains a powder of a lower alkyl(meth)acrylate polymer, the liquid material contains a liquid plasticizer, and the final form of the powder material and the liquid material changing into the pasty form is an elastic body. The elastic body can be applied effectively to a tissue conditioner.

The powder contained in the powder material of the dental powder/liquid material preferably has a specific surface area, as measured by the nitrogen adsorption BET method based on ISO 9277:2010 (hereinafter referred to as "BET method"), of 0.01 to 20 $m^2/g$, and a bulk density, as measured in accordance with JIS K7365:1999 (hereinafter referred to as "JIS K7365"), of 0.1 to 1.0 $g/cm^3$. The powder with the above specific surface area and bulk density, when mixed with the liquid material, is excellent in contactability, is easily soluble in the liquid material, promptly increases in viscosity at an initial stage, and has satisfactory workability as a dental material. On the other hand, it is apt to take air into its particle voids, and the problem of air remaining in a final product obtained by mixing the liquid material and the powder material occurs particularly remarkably. Hence, the air intake preventing effect by the adoption of the preparation accommodation bag of the present invention is exhibited even more satisfactorily. In this respect as well, the present invention is preferred.

Furthermore, the object of the present invention is attained by a dispensing method for a dental powder/liquid material-containing preparation accommodation bag, comprising: accommodating a powder material in a first accommodation chamber of a bag body; accommodating a liquid material in a second accommodation chamber partitioned from the first accommodation chamber by a weakened section, the liquid material dissolving the powder material and changing into a pasty form in cooperation with the powder material; rupturing the weakened section by application of a pressing force to the bag body, thereby bringing the first accommodation chamber and the second accommodation chamber into communication, to feed the liquid material accommodated in the second accommodation chamber into the first accommodation chamber; then mixing the powder material and the liquid material within the first accommodation chamber; and pressing the powder material and the liquid material, which change into the pasty form, from the surfaces of the bag body for dispensing.

Effects of the Invention

According to the present invention, there is provided a dental powder/liquid material-containing preparation accommodation bag, comprising: a bag body divided into a plurality of parts to form a plurality of sealed accommodation chambers; and a weakened section, formed between the adjacent accommodation chambers, for partitioning the respective accommodation chambers, the weakened section being formed to be rupturable by a pressing force applied to the bag body, the accommodation chambers being allowed to communicate after rupture of the weakened section, whereby contents accommodated in the accommodation chambers can be gathered within one of the accommodation chambers and can be mixed there, wherein the bag body is configured such that the plurality of accommodation chambers accommodate a dental powder/liquid material composed of a powder material containing an organic polymer, and a liquid material dissolving the powder material and changing into a pasty form in cooperation with the powder material, with the powder material and the liquid material being accommodated separately in the respective accommodation chambers, and the powder material and the liquid material changing into the pasty form after rupture of the weakened section can be pressed via the surface of the bag body. Since contact with outside air is restricted because of these features, the amount of air bubbles incorporated can be decreased, and the amount of entrained air can be decreased. Consequently, the rate of internal polymerization can be raised. Furthermore, air held in the particle voids can be pushed out of the materials converted into the pasty form by the pressing force applied via the surfaces of the bag body during mixing. Because of this air release, the quality of the dispensed contents can be improved.

MODE FOR CARRYING OUT THE INVENTION

A dental powder/liquid material-containing preparation accommodation bag, and a dispensing method therefor, in an embodiment of the present invention will be described with reference to the accompanying drawings.

Figure 1:
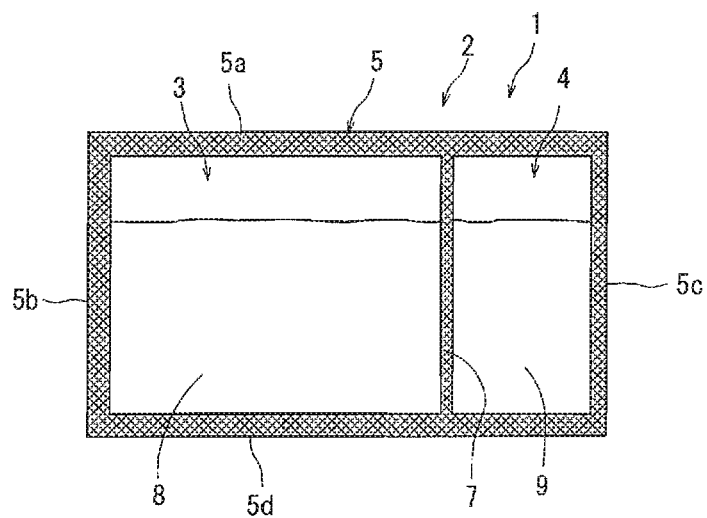
FIG. 1 is a front view of a preparation accommodation bag in an embodiment of the present invention.
Figure 2:
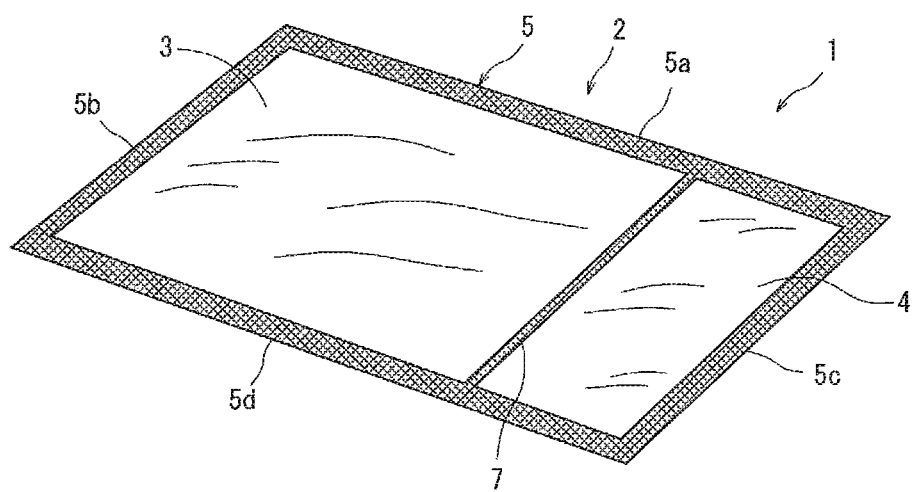
FIG. 2 is a perspective view of the preparation accommodation bag in the embodiment of the present invention.

FIGS. 1 and 2 show a dental powder/liquid material-containing preparation accommodation bag 1 according to the embodiment of the present invention.

The preparation accommodation bag 1 is formed from a bag body 2, and its shape is rectangular in the present embodiment. The bag body 2 is formed by superposing transparent or translucent film sheets. If the bag body 2 is used with prints thereon, it is preferred to provide a transparent or translucent portion in it so that its interior can be observed.

The bag body 2 is divided into a powder material accommodation chamber 3 accommodating a powder material, and a liquid material accommodation chamber 4 accommodating a liquid material, and the accommodation chambers 3 and 4 are adjacent to each other. These accommodation chambers 3, 4 are each preferably quadrilateral, but other shape can be used unless it does not impede mixing. Also, the corners of each chamber can be processed into a round shape in order to increase the efficiency of mixing. The peripheral edge 5 of the bag body 2 is sealed by thermal welding in a predetermined width. Between the powder material accommodation chamber 3 and the liquid material accommodation chamber 4 located adjacently, partition wall 7 for partitioning them is formed. In the present embodiment, the partition wall 7 is formed by thermal welding, but defines a weakened section welded weakly as compared with thermal welding at the peripheral edge 5 of the bag body 2. The weakened section is formed to have such strength that the partition wall 7 is ruptured, for example, upon application of pressing force to the liquid material accommodation chamber 4 when the powder material is accommodated in the powder material accommodation chamber 3, and the liquid material is accommodated in the liquid material accommodation chamber 4. The peripheral edge 5 subjected to thermal welding, on the other hand, has such strength as not to be ruptured against the pressing force.

As the material for the bag body 2, a hard material which cannot deform is excluded, and the material may differ according to the type of the powder material or the liquid material accommodated in the accommodation chamber 3 or 4. Generally, however, various materials having such strength as not to be easily rupturable can be used. For example, synthetic resins such as polyethylene, polypropylene, polyester, polyamide, and ethylene-vinyl acetate, and an aluminum film can be used singly or as a mixture in the form of a sheet. Alternatively, a laminate sheet composed of two or more sheets laminated can be used. The thickness of the sheet is preferably 40 to 200 μm.

Under the procedures for formation of the preparation accommodation bag 1, two films are superposed, or one sheet is folded, to form a two-layer film. If the film is a continuous sheet, it is cut into a size corresponding to the single bag body 2, and thermally welded on right and left sides 5b, 5c, a lower side 5d, and the partition wall 7. From an upper side 5a of the bag body 2 which is open at this point in time, a desired amount of a powder material 8 is accommodated into the powder material accommodation chamber 3. Similarly, from the upper side 5a, a desired amount of a liquid material 9 is accommodated into the liquid material accommodation chamber 4. In the present embodiment, after a predetermined amount of air is incorporated into the powder material accommodation chamber 3 and/or the liquid material accommodation chamber 4, the upper side 5a of the bag body 2 is thermally welded. Thus, the entire periphery of the bag body 2 is sealed, and the partition wall 7 maintains sealing properties. Hence, the two accommodation chambers 3 and 4 are each formed in a sealed state.

An example of a method for using the dental powder/liquid material-containing preparation accommodation bag 1 will be described.

If its uses are a denture base liner, a dental repair resin, and a dental resin cement, it is preferred for the powder material to contain a powder of a lower alkyl(meth)acrylate polymer, for the liquid material to contain a monomer, and for at least one of the powder material and the liquid material to contain a polymerization initiator. The polymerization initiator is usually mixed with the powder material.

In detail, in the case of the denture base liner and the dental repair resin, a (meth)acrylate polymer, such as a polyethyl methacrylate polymer, a poly(methyl methacrylate-ethyl methacrylate)copolymer, or a polymethyl methacrylate polymer, is used as the powder material. A (meth)acrylate monomer, such as methyl methacrylate, acetoacetoxyethyl methacrylate, or 1,9-nonanediol dimethacrylate, is used as the liquid material. As the polymerization initiator, benzoyl peroxide, dimethyl-p-toluidine, 1-cyclohexyl-5-ethylpyrimidinetrione, dilauryldimethylammonium chloride, or acetylacetone copper or the like is used.

If the use is the dental resin cement, a poly(methyl methacrylate-ethyl methacrylate)copolymer or the like is used as the powder material. A (meth)acrylate monomer, such as methyl methacrylate, hydroxyethyl methacrylate, or urethane dimethyl dimethacrylate, is used as the liquid material. Tetraphenylboron triethanolamine salt, dibutylhydroxytoluene, or sodium p-toluenesulfinate is used as the polymerization initiator.

In the case of the tissue conditioner as the use, it is preferred that the powder material contains a powder of a lower alkyl(meth)acrylate polymer, the liquid material contains a liquid plasticizer, and the final form of the powder material and the liquid material changing into a paste is an elastic body. In detail, a (meth)acrylate polymer, such as a polybutyl methacrylate polymer or a polyethyl methacrylate polymer, is used as the powder material. A liquid plasticizer such as diethyl sebacate or diethyl phthalate is used as the liquid material. The liquid plasticizer may be a polymeric plasticizer such as polybutyl acrylate or polypropyl acrylate.

The powder of a lower alkyl(meth)acrylate polymer, used as the powder material, is excellent in polymerizability, imparts high mechanical strength to a cured product, and is satisfactory in solubility in the monomer. Thus, its specific surface area is preferably in the range of 0.01 to 20 m$^2$/g, more preferably in the range of 0.05 to 15 m$^2$/g. The specific surface area is a value measured by the nitrogen adsorption BET method. For the same reasons, the powder of a lower alkyl(meth)acrylate polymer has a bulk density of preferably 0.1 to 1.0 g/cm$^3$, more preferably 0.15 to 0.8 g/cm$^3$. The bulk density is a value measured in accordance with JIS K7365.

The powder having a specific surface area and a bulk density in excess of the above upper limit values results in a viscosity rise too quick when the powder material and the liquid material are mixed. Thus, the operator has difficulty in obtaining a sufficient operating time. Moreover, the effect of preventing air intake into the paste tends to lower slightly. The powder having a specific surface area and a bulk density short of the above lower limit values, on the other hand, leads to rough particles, and insufficient solubility in the liquid material, in dental applications.

Figure 3:
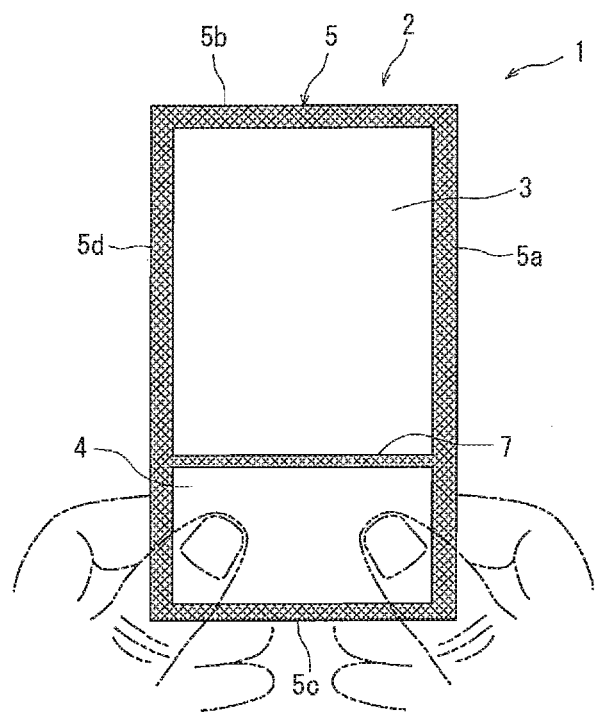
FIG. 3 is a front view showing procedures for use of the preparation accommodation bag in the embodiment of the present invention, in which a liquid material accommodation chamber is pressed to rupture a partition wall.
Figure 4:
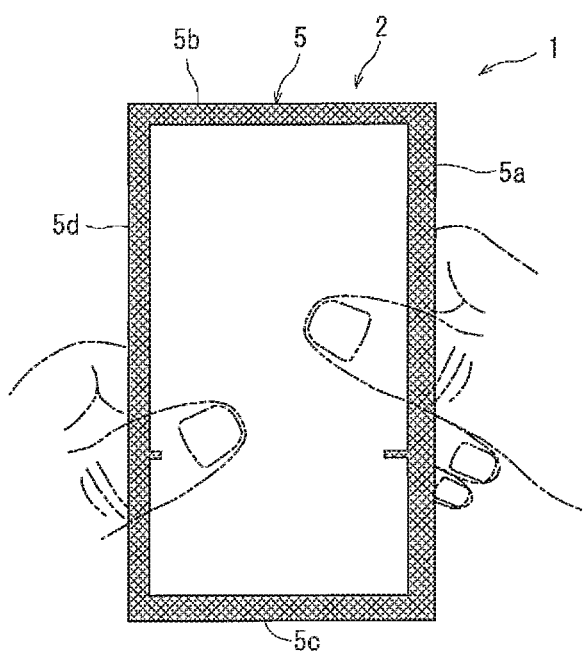
FIG. 4 is a front view showing the procedures for use of the preparation accommodation bag in the embodiment of the present invention, in which a mixture is pressed via a bag body.

As shown in FIG. 3, the dentist or the like takes the preparation accommodation bag 1 manually, and grasps it so as to hold the liquid material accommodation chamber 4, which accommodates the liquid material 9, between the thumbs and index fingers of both hands. Then, the dentist or the like presses the liquid material accommodation chamber 4 so that the liquid material 9 in the liquid material accommodation chamber 4 is pushed in toward the powder material accommodation chamber 3. On this occasion, the partition wall 7 as the weakened section is entirely or partly ruptured under the hydraulic pressure of the liquid material 9 and the pneumatic pressure of air contained therein by push-in of the liquid material accommodation chamber 4. Upon rupture of the partition wall 7, the liquid material 9 is infiltrated so as to be absorbed by the powder material 8. Then, as shown in FIG. 4, the dentist or the like presses a mixture of the liquid material 9 and the powder material 8 while pressing the surfaces (including front, back, both front and back) of the bag body 2 using the thumbs and the index fingers. A recommendable way of pressing is to press the bag body 2 so as to bring the mixture toward any one side thereof.

The mixture turns into a highly flowable slurry owing to a dissolution action or the like, and gradually increases in viscosity, becoming pasty, with the progress of dissolution, the progress of a chemical reaction, and so on.

The pressing operation for the mixture does not entrain air from outside the bag into the mixture, unlike kneading or stirring hitherto carried out, but conversely, exhibits the effect of forcing bubbles of air contained in the mixture out of the mixture.

Figure 5:
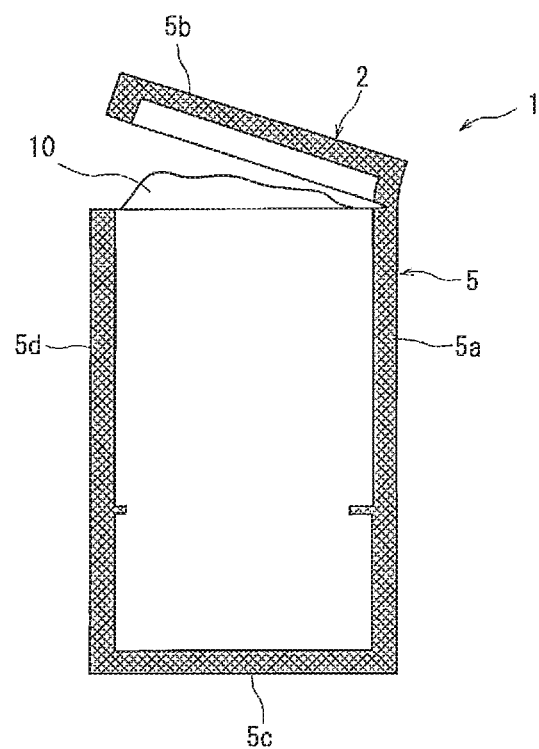
FIG. 5 is a front view showing the procedures for use of the preparation accommodation bag in the embodiment of the present invention, in which a dental material in a pasty form is withdrawn from the bag body.

As shown in FIG. 5, the dentist or the like cuts any part of the bag body 2 at a time when the mixture becomes appropriately soft (in about 1 to 5 minutes) enough to be processible for an operation to be performed using the mixture. Then, the dentist or the like withdraws a pasty material 10 while pushing it out of the bag body 2. The material 10 withdrawn from the bag body 2 is formed into a desired shape, and finally cured at a diseased area of a patient, or converted into an elastic body by the action of the plasticizer.

Such a dental material is directly applied for treatment to the patient in the dental examination room, or is used for operation, with the patient waiting in a waiting room. Thus, its handling is required to be completed in a short time for prompt treatment. In the present embodiment, dispensing can be started at rupture of the partition wall 7 of the preparation accommodation bag 1. Thus, the conventional labor of charging suitable amounts of the powder material and the liquid material into a blending cup can be saved, and the operating time until obtainment of a suitable viscosity is of the order of 1 minute to 5 minutes.

Conventionally, the mixture has been mixed using a spatula, so that the entrainment of air bubbles can be somewhat prevented by the operator's skill, etc. In the present embodiment, a dental material with few air bubbles can be always obtained regardless of the skill. Moreover, air taken between the particle gaps or voids of the powder can also be forced out of the paste by the pressing force exerted via the surfaces of the bag body at the time of mixing.

Other characteristics required of dental materials are miscibility, quick viscosity increase, handleability, easy shapability, and prompt curing. In these respects as well, the dental material of the present invention causes no hindrance, and rivals or exceeds conventional dental materials.

EXAMPLES

Next, test examples concerned with the present embodiment will be described, but the present invention is in no way limited by the following test examples.

Using the above-described preparation accommodation bag, a denture base liner and a dental repair resin (Test Example 1), a tissue conditioner (Test Example 2), and a dental resin cement (Test Example 3) were dispensed, and compared with conventional methods.

Test Example 1: Test for Dispensing of Denture Base Liner and Dental Repair Resin

[Materials Used]
(1) The following materials were used as powder materials:
Polyethyl methacrylate polymer (PEMA)
Particle size 35 μm: specific surface area 0.3 m$^2$/g, bulk density 0.68 g/cm$^3$ (supplier: Sekisui Plastics Co., Ltd.: EMA35)
Particle size 10 μm: specific surface area 0.4 m$^2$/g, bulk density 0.48 g/cm$^3$ (supplier: Sekisui Plastics Co., Ltd.: EMA10)
Poly (methyl methacrylate-ethyl methacrylate)copolymer (P(MMA-EMA))
Particle size 80 μm: specific surface area 0.05 m$^2$/g, bulk density 0.75 g/cm$^3$ (supplier: Negami Chemical Industrial Co., Ltd.: D100)
Particle size 30 μm: specific surface area 0.3 m$^2$/g, bulk density 0.63 g/cm$^3$ (supplier: Negami Chemical Industrial Co., Ltd.: D200)
Polymethyl methacrylate polymer (PMMA)
Particle size 20 μm: specific surface area 0.2 m$^2$/g, bulk density 0.51 g/cm$^3$ (supplier: Negami Chemical Industrial Co., Ltd.: D250ML)
Particle size 4 μm: specific surface area 0.8 m$^2$/g, bulk density 0.34 g/cm$^3$ (supplier: Negami Chemical Industrial Co., Ltd.: D350ML-3A)
Particle size 0.2 μm: specific surface area 15 m$^2$/g, bulk density 0.18 g/cm$^3$ (supplier: Soken Chemical & Engineering Co., Ltd.: MP1451)
(2) The following materials were used as liquid materials:
Methyl methacrylate (MMA) (supplier: Wako Pure Chemical Industries, Ltd.)
Acetoacetoxyethyl methacrylate (AAEM) (supplier: Nippon Synthetic Chemical Industry Co., Ltd.)
1,9-Nonanediol dimethacrylate (ND) (supplier: Shin-Nakamura Chemical Co., Ltd.)
(3) The following materials were used as polymerization initiators:
Benzoyl peroxide (BPO) (supplier: Wako Pure Chemical Industries, Ltd.)
Dimethyl-p-toluidine (DMPT) (supplier: Tokyo Chemical Industry Co., Ltd.)
1-Cyclohexyl-5-ethylpyrimidinetrione (CEPT)
Dilauryldimethylammonium chloride (LMAC) (supplier: TAKEMOTO OIL & FAT CO., LTD.)
Acetylacetone copper (ACu) (supplier: Wako Pure Chemical Industries, Ltd.)

The methods for preparation of the powder material and the liquid material were as follows:

The powder material in Examples 1 to 9 and Comparative Example 1 was obtained by adding 1 part by weight of EPO, as a polymerization initiator component, to 100 parts by weight of PEMA35. The liquid material in these examples was obtained by adding 20 parts by weight of ND and 0.3 part by weight of DMPT, as a polymerization initiator component, to 80 parts by weight of AAEM.

The powder material in Example 10 was prepared in the same manner as above, except that PEMA35 in Examples 1 to 9 was replaced by PEMA10. The liquid material in this example was prepared in the same manner as above.

The powder material in Examples 11, 12 and Comparative Example 2 was prepared in the same manner as above, except that PEMA35 in Examples 1 to 9 was replaced by PEMA10 or P (MMA-EMA) The liquid material in these examples was prepared in the same manner as above, except that MMA was used as a substitute.

The powder material in Examples 13 to 16 was obtained by adding 1.5 parts by weight of CEPT and 0.01 part by weight of ACu to 100 parts by weight of the powder component shown in Table 1. The liquid material therein was obtained by adding 0.03 part by weight of LMAC to 100 parts by weight of MMA.

Reference Example 1 concerns a curable material composed of two liquid materials. One of the liquid materials was obtained by adding 1 part by weight of BPO to 100 parts by weight of AAEM. The other liquid material was obtained by adding 40 parts by weight of ND and 0.3 part by weight of DMPT to 60 parts by weight of AAEM.

In connection with the testing methods, the mixing method X shown in Table 1 represents dispensing using the preparation accommodation bag of the present invention, while the mixing method Y represents a method which comprises weighing the powder and the liquid into a blending cup, and blending them in an open state with the use of a spatula, as in customary practice.

The void ratio shown in Table 1 was determined by the percentage of the void volume to the internal volume of the powder material accommodation chamber 3 where the liquid material is fed in and mingled with the powder material.

Void ratio(%)=void volume/internal volume of powder material accommodation chamber×100

The void volume was determined by a volume obtained by subtracting the total volume of the charged powder material and liquid material from the internal volume of the powder material accommodation chamber measured beforehand.

Void volume=internal volume of powder material accommodation chamber−(volume of powder material+volume of liquid material)

The volume of the powder material was calculated by dividing the weight of the powder material by its bulk density (powder material weight/bulk density), whereas the volume of the liquid material was calculated by dividing the weight of the liquid material by the specific gravity of the liquid (liquid material weight/liquid specific gravity).

The air bubble incorporation in Table 1 was evaluated by observing with a magnifying glass air bubbles confirmed on the surface of a cured product/elastic body measuring 6 mm (diameter)×1 mm, voids generated in the presence of fine air bubbles, or blushed regions; and finding the proportion of their area to the total area. In preparing the cured product, the liquid was confirmed to have spread throughout the powder, whichever method of mixing was adopted. Then, the system was blended for a further period of 5 seconds, and a proper amount of the blend was poured into a mold or the like having a hole of the above size. The blend poured in was allowed to stand without pressure contact, cured, and then flattened on the surface using a waterproof abrasive paper (No. 800). An air bubble incorporation rate of less than 10% was evaluated as A, a value of 10% or more, but less than 20% was evaluated as B, a value of 20% or more, but less than 30% was evaluated as C, and a value of 30% or more was evaluated as D. Less air bubble incorporation gained a higher evaluation.

For the flexural strength in Table 1, a mold having a rectangular hole with a width of 4 mm, a thickness of 2 mm, and a length of 40 mm was charged with a curable material, which was cured in the same manner as in the measurement of the unpolymerized amount. The resulting cured product was subjected to a flexural test using a strength tester. Under the following conditions, a crosshead speed of 1 mm/min, and a spanning distance of 15 mm, a 3-point bending test was conducted to find the flexural strength.

The color test (resistance to discoloration) in Table 1 was conducted in the following manner: A cured product measuring 10 mm×10 mm×2 mm was prepared, stored for 2 hours in water at 37° C., and then measured for (L*), (a*), and (b*) before coloration by means of a color difference meter. Then, the specimen was immersed in a 5 wt. % aqueous solution of coffee, and stored for 24 hours at 40° C. with stirring. After storage, the specimen was washed with water, dried, and then measured again for (L*), (a*), and (b*) by means of the color difference meter. Using the differences (ΔL*) (Δa*), and (Δb*) between those parameters before and after the color test, the amount of color (ΔE*) was calculated from the following equation:

Amount of color $(\Delta E^*) = \{(\Delta L^*)^2 + (\Delta a^*)^2 + (\Delta b^*)^2\}^{1/2}$ The difference (ΔL*) represents a difference in brightness, and the differences (Δa*) and (Δb*) represent differences in color chroma. The lower the value of (ΔE*), the smaller change in color differences.

The results of the test are shown in Table 1.

TABLE 1

| | Powder material | | | Liquid material | Polymerization initiator |
| --- | --- | --- | --- | --- | --- |
| | Type | Particle size (μm) | Specific surface area (m²/g) | Type | Type |
| Ex. 1 | PEMA | 35 | 0.3 | AAEM/ND | BPO/DMPT |
| Ex. 2 | ↑ | ↑ | ↑ | ↑ | ↑ |
| Ex. 3 | ↑ | ↑ | ↑ | ↑ | ↑ |
| Ex. 4 | ↑ | ↑ | ↑ | ↑ | ↑ |
| Ex. 5 | ↑ | ↑ | ↑ | ↑ | ↑ |
| Ex. 6 | ↑ | ↑ | ↑ | ↑ | ↑ |
| Ex. 7 | ↑ | ↑ | ↑ | ↑ | ↑ |
| Ex. 8 | ↑ | ↑ | ↑ | ↑ | ↑ |
| Ex. 9 | ↑ | ↑ | ↑ | ↑ | ↑ |
| Ex. 10 | ↑ | 10 | 0.4 | ↑ | ↑ |
| Ex. 11 | P(MMA-EMA) | 80 | 0.05 | MMA | BPO/DMPT |
| Ex. 12 | ↑ | 30 | 0.3 | ↑ | ↑ |
| Ex. 13 | ↑ | ↑ | ↑ | ↑ | CEPT/ACu/LMAC |
| Ex. 14 | PMMA | 20 | 0.2 | ↑ | ↑ |
| Ex. 15 | ↑ | 4 | 0.8 | ↑ | ↑ |
| Ex. 16 | ↑ | 0.2 | 15 | ↑ | ↑ |
| Comp. Ex. 1 | PEMA | 35 | 0.3 | AAEM/ND | BPO/DMPT |
| Comp. Ex. 2 | P(MMA-EMA) | 80 | 0.05 | MMA | ↑ |
| Ref. Ex. 1 | | | | Liquid material (1) AAEM/BPO Liquid material (2) AAEM/ND/DMPT | |

| | Mixing method | Void ratio (%) | Air bubble incorporation | Flexural strength (MPa) | Color test ΔE |
| --- | --- | --- | --- | --- | --- |
| Ex. 1 | X | 5 | A | 77 | 1.1 |
| Ex. 2 | ↑ | 8 | A | 78 | 1.2 |
| Ex. 3 | ↑ | 10 | A | 80 | 1.1 |
| Ex. 4 | ↑ | 15 | A | 81 | 1.1 |
| Ex. 5 | ↑ | 20 | A | 80 | 0.9 |
| Ex. 6 | ↑ | 30 | A | 80 | 0.8 |
| Ex. 7 | ↑ | 40 | A | 81 | 0.9 |
| Ex. 8 | ↑ | 45 | B | 74 | 1.6 |
| Ex. 9 | ↑ | 60 | C | 69 | 2.1 |
| Ex. 10 | ↑ | 30 | A | 80 | 1.1 |

TABLE 1-continued

| | | | | | |
|---|---|---|---|---|---|
| Ex. 11 | ↑ | 30 | A | 89 | 0.6 |
| Ex. 12 | ↑ | ↑ | A | 90 | 0.6 |
| Ex. 13 | ↑ | ↑ | A | 91 | 0.5 |
| Ex. 14 | ↑ | ↑ | A | 89 | 0.8 |
| Ex. 15 | ↑ | ↑ | A | 89 | 0.7 |
| Ex. 16 | ↑ | ↑ | B | 79 | 1 |
| Comp. Ex. 1 | Y | — | D | 55 | 3.8 |
| Comp. Ex. 2 | ↑ | — | D | 59 | 3.6 |
| Ref. Ex. 1 | ↑ | — | A | — | — |

Reference to Table 1 shows that the proportions of the materials were the same, and the same conditions (excluding the void ratio) were adopted except for the mixing method, in Examples 1 to 9 and Comparative Example 1. It is seen in Table 1, however, that the results in all cases, including air bubble incorporation, were better in Examples 1 to 9 using the preparation accommodation bag of the present invention than in Comparative Example 1.

Similarly, it is seen that the proportions of the materials were the same, and the same conditions were adopted except for the mixing method, in Example 11 and Comparative Example 2, but that the results in all cases were better in Example 11 using the preparation accommodation bag of the present invention than in Comparative Example 2.

From Examples 1 to 9, moreover, it is noted that changes in the void ratio led to differences in the air bubble incorporation, flexural strength, and color effect, thus influencing the quality. Besides, the air bubble incorporation in the range of less than 10% corresponded to the void ratio in the range of 5 to 40%.

The flexural strength was 55 to 59 MPa in the conventional method, and 69 to 91 MPa in the Examples of the present invention. These findings confirmed that the strength of the cured product in the final form was greatly enhanced in the present invention. Moreover, a decline in discoloration (improvement in discoloration resistance) was observed in the present invention.

From Reference Example 1, it was observed that when liquid materials were mixed by the conventional method, incorporation of air bubbles was minimal, unlike the use of a powder-liquid mixture material. This findings showed that when a powder material and a liquid material were mixed, air bubbles were incorporated more easily than when liquid materials were mixed.

Test Example 2: Test for Dispensing of Denture Tissue Conditioner

[Materials Used]
(1) The following materials were used as powder materials:
Polybutyl methacrylate polymer (PBMA)
Particle size 40 μm: specific surface area 0.3 m²/g (supplier: Negami Chemical Industrial Co., Ltd.: D200B)
Polyethyl methacrylate polymer (PEMA)
Particle size 35 specific surface area 0.3 m²/g (supplier: Sekisui Plastics Co., Ltd.: EMA35)
(2) The following materials were used as liquid materials:
Polybutyl acrylate (PEA): Synthetic product
Polypropyl acrylate (PPA): Synthetic product
Diethyl sebacate (SE) (supplier: Wako Pure Chemical Industries, Ltd.)
As powder materials and liquid materials in Examples 17 to 28 and Comparative Examples 3 to 5, the powder material and liquid material components shown in Table 2 were used singly as such.

In connection with test samples, X in the mixing method shown in Table 2 represents the one dispensed using the preparation accommodation bag of the present invention, while Y in the mixing method represents that obtained by weighing the powder and the liquid into a blending cup, and blending them in an open state with the use of a spatula, as by a conventional method.

The void ratio and the air bubble incorporation shown in Table 2 were evaluated by the same methods as in the aforementioned Test Example 1.

The results of the test are shown in Table 2.

TABLE 2

| | Powder material | | | | | | |
|---|---|---|---|---|---|---|---|
| | Type | Particle size (μm) | Specific surface area (m²/g) | Liquid material Type | Mixing method | Void ratio (%) | Air bubble incorporation |
| Ex. 17 | PBMA | 40 | 0.3 | PBA | X | 5 | A |
| Ex. 18 | ↑ | ↑ | ↑ | ↑ | ↑ | 8 | A |
| Ex. 19 | ↑ | ↑ | ↑ | ↑ | ↑ | 10 | A |
| Ex. 20 | ↑ | ↑ | ↑ | ↑ | ↑ | 15 | A |
| Ex. 21 | ↑ | ↑ | ↑ | ↑ | ↑ | 20 | A |
| Ex. 22 | ↑ | ↑ | ↑ | ↑ | ↑ | 30 | A |
| Ex. 23 | ↑ | ↑ | ↑ | ↑ | ↑ | 40 | A |
| Ex. 24 | ↑ | ↑ | ↑ | ↑ | ↑ | 45 | B |
| Ex. 25 | ↑ | ↑ | ↑ | ↑ | ↑ | 60 | C |
| Ex. 26 | ↑ | ↑ | ↑ | PPA | ↑ | 30 | A |
| Ex. 27 | ↑ | ↑ | ↑ | SE | ↑ | ↑ | A |
| Ex. 28 | PEMA | 35 | 0.3 | SE | ↑ | ↑ | A |
| Comp. Ex. 3 | PBMA | 40 | 0.3 | PBA | Y | — | D |
| Comp. Ex. 4 | ↑ | ↑ | ↑ | PPA | ↑ | — | D |
| Comp. Ex. 5 | ↑ | ↑ | ↑ | SE | ↑ | — | D |

Reference to Table 2 shows that the same conditions (excluding the void ratio) were adopted except for the mixing method, in Examples 17 to 25 and Comparative Example 3. It is seen in Table 2, however, that Examples 17 to 25 using the preparation accommodation bag of the present invention were better than Comparative Example 3 in terms of less incorporation of air bubbles. Besides, the air bubble incorporation in the range of less than 10% corresponded to the void ratio in the range of 5 to 40%.

Test Example 3: Test for Dispensing of Dental Resin Cement

[Materials Used]
(1) The following materials were used as powder materials:
Poly(methyl methacrylate-ethyl methacrylate)copolymer (P(MMA-EMA))
Particle size 30 μm: specific surface area 0.3 m²/g (supplier: Negami Chemical Industrial Co., Ltd.: D200)

Pulverized polymethyl methacrylate polymer (PMMA1) Particle size 20 μm (synthetic product of Tokuyama Dental Corp.: For the method of synthesis, see Japanese Patent No. 5110923)

Sulfonate-containing acidic resin (SP-01) (synthetic product of Tokuyama Dental Corp.: For the method of synthesis, see Japanese Patent No. 5110923)

Fluoroaluminosilicate glass filler (FASG) (supplier: Tokuyama Dental Corp.: basicity-abated product: For the method of abating treatment, see Japanese Patent No. 3669563)

γ-Methacryloxypropyltrimethoxysilane-treated spherical silica-zirconia filler (G1) Particle size 0.52 μm (synthetic product of Tokuyama Dental Corp.)

(2) The following materials were used as liquid materials:

Methyl methacrylate (MMA) (supplier: Wako Pure Chemical Industries, Ltd.)

Hydroxyethyl methacrylate (HEMA) (supplier: Wako Pure Chemical Industries, Ltd.)

Urethanedimethyl dimethacrylate (UDMA) (supplier: KYOEISHA CHEMICAL CO., LTD.)

(3) The following materials were used as polymerization initiators/inhibitors:

Tetraphenylboron triethanolamine salt (PhBTEOA) (supplier: Wako Pure Chemical Industries, Ltd.)

Dibutylhydroxytoluene (BHT) (supplier: Tokyo Chemical Industry Co., Ltd.)

Sodium p-toluenesulfinate (pTsNa)

(4) The following materials were used as pretreatment materials:

Mixture of 2-methacryloyloxyethyl dihydrogen phosphate and bis(2-methacryloyloxyethyl)hydrogen phosphate (PM) Bis(maltolato)oxovanadium (IV) (BMOV) (supplier: Sigma-Aldrich Corporation)

Urethanedimethyl dimethacrylate (UDMA) (supplier: KYOEISHA CHEMICAL CO., LTD.)

Acetone (supplier: Wako Pure Chemical Industries, Ltd.)

Isopropanol (IPA) (supplier: Wako Pure Chemical Industries, Ltd.)

The methods for preparation of the powder materials and the liquid materials were as follows:

The powder material in Example 29 and Comparative Example 6 was obtained by adding 5 parts by weight of SP-01 to a resin powder mixture (for the powder material) composed of 60 parts by weight of PMMA-EMA1 and 40 parts by weight of PMMA1. The liquid material in these examples was obtained by adding 4 parts by weight of PhBTEOA to a polymerizable monomer mixture (for the liquid material) composed of a mixture of 80 parts by weight of MMA, 10 parts by weight of HEMA, 10 parts by weight of UDMA, and 0.1 part by weight of BHT.

The powder material in Example 30 and Comparative Example 7 was obtained by mixing 100 parts by weight of FASG, 10 parts by weight of G1, 0.5 part by weight of BPO, and 1 part by weight of pTSNa. The liquid material in these examples was obtained by mixing 100 parts by weight of PM, 250 parts by weight of HEMA, 150 parts by weight of UDMA, and 0.5 part by weight of DMPT.

The pretreatment material used in Example 29 and Comparative Example 6 was obtained by adding 0.2 part by weight of BMW to 20 parts by weight of PM, 30 parts by weight of water, 5 parts by weight of UDMA, 35 parts by weight of acetone, and 10 parts by weight of IPA.

In connection with test samples, X in the mixing method shown in Table 3 represents the one dispensed using the preparation accommodation bag of the present invention, while Y in the mixing method represents that obtained by weighing the powder and the liquid into a blending cup, and blending them in an open state with the use of a spatula, as in customary practice.

The void ratio and the air bubble incorporation shown in Table 3 were evaluated by the same methods as in the aforementioned Test Example 1.

The adhesive force in Table 3 was investigated in the following manner: A bovine front tooth was extracted within 24 hours after slaughter and, with water being poured thereover, it was sanded down with a #800 emery paper to expose the enamel or dentinal plane so as to be parallel to the labial surface. Then, compressed air was blown against this plane for about 10 seconds to dry it. Then, a double-coated tape having a hole of 3 mm in diameter was secured to the plane to form a simulated cavity. Within the simulated cavity, a dental primer was coated on the tooth surface, and allowed to stand for 20 seconds. Then, compressed air was blown against it for about 5 seconds. Then, the dental adhesive of the Example or the Comparative Example was charged into the simulated cavity, whereafter a stainless attachment with a diameter of 8 mm was pressure-contacted therewith to prepare an adhesion test piece. The adhesion test piece was immersed in water at 37° C. for 24 hours, and then the strength of its adhesion to the tooth was measured at a crosshead speed of 1 mm/min with the use of a tensile tester (Autograph, produced by Shimadzu Corporation).

The results of the test are shown in Table 3.

TABLE 3

| | Powder material | | | | | Void | | Adhesive |
| | Type | Particle size (μm) | Specific surface area | Liquid material Type | Mixing method | ratio (%) | Air bubble incorporation | force (MPa) |
| --- | --- | --- | --- | --- | --- | --- | --- | --- |
| Ex. 29 | P(MMA-EMA) | 30 | 0.3 | MMA/HEMA/UDMA | X | 30 | A | 29.3 |
| Ex. 30 | FASG | | | HEMA/UDMA | ↑ | 30 | A | 18.1 |
| Comp. Ex. 6 | P(MMA-EMA) | 40 | 0.3 | MMA/HEMA/UDMA | Y | — | D | 22.0 |
| Comp. Ex. 7 | FASG | | | HEMA/UDMA | ↑ | — | D | 11.3 |

Reference to Table 3 shows that the particle size was different between Examples 29, 30 and Comparative Examples 6, 7, but Examples 29, 30 using the preparation accommodation bag of the present invention were better than Comparative Examples 6, 7 in terms of less incorporation of air bubbles. Besides, the adhesive force was 22.0 MPa in Comparative Example 6 and 29.3 MPa in Example 29, while it was 11.3 MPa in Comparative Example 7 and 18.1 MPa in Example 30. These findings show the product dispensed using the preparation accommodation bag had greater adhesive force.

The results of Tests 1 to 3 show the following:

In connection with the denture base liner, the dental repair resin, the tissue conditioner, and the dental resin cement, the mixing method X showed marked decreases in the amount of air bubbles incorporated as compared with the mixing method Y.

The flexural strength was clearly higher in the Examples than in the Comparative Examples, as seen from Table 1. A primary factor in enhancing the adhesive strength is considered to be an increase in the rate of internal polymerization ascribed to a decrease in air bubble incorporation due to absence of contact with outside air, and a decrease in the amount of entrained air.

The present invention has been described in detail above based on the embodiment with reference to the accompanying drawings. However, the present invention is in no way limited to the foregoing embodiment, but other changes or modifications can be made without departing from the scope of the invention.

In the above embodiment, for example, the bag body 2 is divided into the powder material accommodation chamber 3 and the liquid material accommodation chamber 4. However, the bag body 2 may be divided into three or more accommodation chambers, and the contents of these accommodation chambers may be mixed together.

In the above-described embodiment, the preparation accommodation bag is shaped like a sheet with a small thickness, but a bag of a three-dimensional structure can be used for practice of the present invention.

EXPLANATION OF LETTERS OR NUMERALS

1 Preparation accommodation bag
2 Bag body
3 Powder accommodation chamber
4 Liquid accommodation chamber
5 Peripheral edge
7 Weakened section
8 Powder material
9 Liquid material

The invention claimed is:

1. A dental powder/liquid material-containing preparation accommodation bag, comprising:
a bag body divided into a plurality of parts to form a plurality of sealed accommodation chambers; and
a weakened section, formed between the accommodation chambers, for partitioning the accommodation chambers, the weakened section being formed to be rupturable by a pressing force applied to the bag body,
the accommodation chambers being allowed to communicate after rupture of the weakened section, whereby contents accommodated in the accommodation chambers can be gathered within one of the accommodation chambers and can be mixed there,
wherein the bag body is configured such that the plurality of accommodation chambers accommodate a powder material containing an organic polymer, and a liquid material dissolving the powder material and changing into a pasty form in cooperation with the powder material being accommodated separately in the accommodation chambers,
wherein a volume of air is incorporated into at least one of the accommodation chambers,
wherein the volume of the air at room temperature is in a range of 15 to 40% based on a total volume of the accommodation chamber for gathering and mixing the contents accommodated within the accommodation chambers,
wherein the powder material and the liquid material changing into the pasty form after rupture of the weakened section can be pressed via surfaces of the bag body, and
wherein
the dental powder/liquid material is in such a configuration that
the powder material contains a powder of a lower alkyl (meth)acrylate polymer,
the liquid material contains a monomer,
at least one of the powder material and the liquid material contains a polymerization initiator, and
a final form of the powder material and the liquid material changing into the pasty form is a cured product.

2. The dental powder/liquid material-containing preparation accommodation bag according to claim 1, wherein
an internal volume of the accommodation chamber for gathering and mixing the contents accommodated within the accommodation chambers is 1 to 3 cm$^3$ relative to 1 g of a pasty substance obtained by blending the powder material and the liquid material.

3. The dental powder/liquid material-containing preparation accommodation bag according to claim 1, wherein
a powder contained in the powder material of the dental powder/liquid material has a specific surface area, as measured by a nitrogen adsorption BET method, of 0.01 to 20 m$^2$/g, and a bulk density, as measured in accordance with JIS K7365, of 0.05 to 1.0 g/cm$^3$.

4. A dental powder/liquid material-containing preparation accommodation bag, comprising:
a bag body divided into a plurality of parts to form a plurality of sealed accommodation chambers; and
a weakened section, formed between the accommodation chambers, for partitioning the accommodation chambers, the weakened section being formed to be rupturable by a pressing force applied to the bag body,
the accommodation chambers being allowed to communicate after rupture of the weakened section, whereby contents accommodated in the accommodation chambers can be gathered within one of the accommodation chambers and can be mixed there,
wherein the bag body is configured such that the plurality of accommodation chambers accommodate a powder material containing an organic polymer, and a liquid material dissolving the powder material and changing into a pasty form in cooperation with the powder material being accommodated separately in the accommodation chambers,
wherein a volume of air is incorporated into at least one of the accommodation chambers,
wherein the volume of the air at room temperature is in a range of 15 to 40% based on a total volume of the accommodation chamber for gathering and mixing the contents accommodated within the accommodation chambers,
wherein the powder material and the liquid material changing into the pasty form after rupture of the weakened section can be pressed via surfaces of the bag body, and
wherein
the dental powder/liquid material is in such a configuration that
the powder material contains a powder of a lower alkyl (meth)acrylate polymer, the liquid material contains a liquid plasticizer, and
a final form of the powder material and the liquid material changing into the pasty form is an elastic body.

5. The dental powder/liquid material-containing preparation accommodation bag according to claim 4, wherein
an internal volume of the accommodation chamber for gathering and mixing the contents accommodated within the accommodation chambers is 1 to 3 $cm^3$ relative to 1 g of a pasty substance obtained by blending the powder material and the liquid material.

6. The dental powder/liquid material-containing preparation accommodation bag according to claim 4, wherein
a powder contained in the powder material of the dental powder/liquid material has a specific surface area, as measured by a nitrogen adsorption BET method, of 0.01 to 20 $m^2/g$, and a bulk density, as measured in accordance with JIS K7365, of 0.05 to 1.0 $g/cm^3$.

* * * * *